United States Patent [19]

Bellas et al.

[11] 4,409,389
[45] Oct. 11, 1983

[54] PREPARATION OF IMIDAZOLES

[75] Inventors: Michael Bellas, Wigan; John Duvall, Liverpool, both of England

[73] Assignee: Eastman Kodak Company, Rochester, N.Y.

[21] Appl. No.: 376,974

[22] Filed: May 10, 1982

Related U.S. Application Data

[63] Continuation of Ser. No. 174,056, Jul. 31, 1980, abandoned.

[30] Foreign Application Priority Data

Jan. 25, 1980 [GB] United Kingdom ............... 8002594

[51] Int. Cl.$^3$ .................. C07D 233/64; C07D 233/58
[52] U.S. Cl. .................................... 548/342; 544/316; 544/333; 546/278; 548/137; 548/152; 548/178; 548/179; 548/180; 548/186; 548/187; 548/189; 548/202; 548/207; 548/209; 548/213; 548/214; 548/335; 548/336
[58] Field of Search ............... 544/316, 333; 546/278; 548/152, 137, 202, 214, 207, 178, 179, 180, 186, 187, 189, 213, 209, 335, 336, 342

[56] References Cited

PUBLICATIONS

Davidson, D., et al., *J. Org. Chem.*, 2, 319, (1937).
Smith, P., *The Chemistry of Open-Chain Organic Nitrogen Compounds*, vol. I, W. A. Benjamin, N.Y., 1965, p. 329.
Knudsen, P., *Berichte*, 2698, (1914).
Lednicer, D., et al., *The Organic Chemistry of Drug Synthesis*, Wiley-Interscience, New York, 1977, vol. 1, pp. 238-241 and vol. 2, pp. 242-249.
Noller, C., *Chemistry of Organic Compounds*, W. B. Saunders, Philadelphia, 1965, p. 523.

*Primary Examiner*—Richard A. Schwartz
*Attorney, Agent, or Firm*—Donald W. Spurrell; Daniel B. Reece, III

[57] ABSTRACT

Disclosed is a novel process and product involving the manufacture in advantageously high yields of imidazole compounds corresponding to the general formula:

$$\begin{array}{c} R_1-C\!=\!\!=\!\!N \\ \| \quad\quad \| \\ R_2-C \quad\quad C-R \\ \diagdown\!\!\!\!N\!\!\!\!\diagup \\ | \\ H \end{array}$$

wherein a preferred embodiment of the process comprises contacting a diamine salt of the formula $$R-CH \begin{array}{c} NH_3^+ \\ \diagup \\ \diagdown \\ NH_3^+ \end{array} \quad 2A^-$$

with a biscarbonyl compound of the structure $$\begin{array}{cc} O & O \\ \| & \| \\ R_1C\!-\!CR_2 \end{array}$$

in an acid medium, wherein R, $R_1$ and $R_2$ each represents hydrogen or any group which does not hinder the cyclization reaction or lead to degradation of the reactants or imidazole products, and $A^-$ is an anion equivalent such as that of mineral acids, sulfonic acids and carboxylic acids.

5 Claims, No Drawings

PREPARATION OF IMIDAZOLES

This is a continuation of application Ser. No. 174,056 filed July 31, 1980 now abandoned.

This invention concerns the manufacture in advantageously high yields of imidazole and substituted imidazoles corresponding to the general formula:

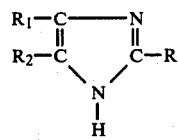

in which R, $R_1$ and $R_2$ each represents any group which does not hinder the cyclization reaction or lead to degradation of the reactants or imidazole products, and may be, for example, hydrogen, an alkyl radical of about 1 to 20 carbon atoms which may be substituted with 1 to 3 of such groups as halogen, hydroxy, alkoxy, alkoxycarbonyl, alkoxycarbonyloxy, carbamoyl, alkylcarbamoyl, dialkylcarbamoyl, arylcarbamoyl, alkylthio, aryl, aryl substituted with 1 to 5 of halogen, alkyl, alkoxy, and the like, cycloaliphatic radicals including, for example, cyclohexyl and cyclohexyl substituted with 1 to 5 of a variety of groups including halogen, alkyl, alkoxy, alkylthio, and the like, heterocyclic radicals which may be substituted with alkyl, thioalkyl and other nonreactive groups, and including thienyl, furfuryl, pyridyl, pyrimidinyl, benzothiazolyl, thiazolyl, isothiazolyl, thiadiazolyl, benzisothiazolyl and indolyl, aryl and aryl substituted with 1 to 5 of halogen, alkyl, alkylthio, or alkoxy, according to the process comprising contacting a methylenediamine salt or substituted methylenediamine salt with a vicinal biscarbonyl compound in an acid medium. The various alkyl or alkylene portions of all of the groups throughout this specification, such as alkoxy, alkylcarbamoyl and the like, contain from 1–10 carbons. More particularly, the process comprises contacting a diamine salt of the formula

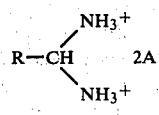

with a biscarbonyl compound of the structure

in an acid system, wherein $A^-$ is an anion equivalent such as that of mono- or multivalent mineral acids, sulfonic acids and carboxylic acids. The term "contacting" means that the reagents are initially in the same reaction system, and no attempt is made herein to theorize the precise reactive species.

Prior methods for the production of imidazole and particularly substituted imidazoles have generally been tedious and result in low yield with significant by-product formation. Such processes include, for example, reacting glyoxal with formaldehyde and ammonia in an aqueous medium; reacting ethylene diamine with formaldehyde in the gas phase over a dehydration catalyst and then with hydrogen over a catalyst containing a noble metal; passing a mixture of ethylene diamine and formic acid over a catalyst containing a metal of the platinum group in the presence of molecular hydrogen in the gas phase at temperatures of from about 300° to 550° C. and then subjecting the condensate collected to fractional distillation; and heating certain N-monoformylalkylene diamines and/or N,N'-diformylalkylene diamines such as N,N'-diformylated-1,2-diaminopropane in gas phase in the presence of zinc oxide at temperatures of from 250° to 800° C. None of these processes give the yields and purities of the present process.

In carrying out the present process, a particularly useful and novel procedure is to form the diamine salt in situ from the corresponding bisamide reactant

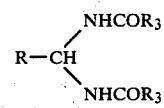

according to the hydrolysis reaction

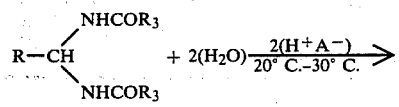

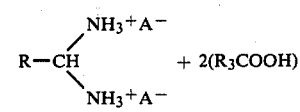

wherein $R_3$ is H or the residue of any acyl group which lends itself to such reaction including those such as alkyl of 1–20 carbons, cycloalkyl, aryl, and such radicals substituted, for example, with alkoxy, alkoxycarbonyl, halogen, alkoxycarbonyloxy, alkylthio, and the like. Of particular utility is the bisamide reactant formed by the reaction of hexamethylenetetramine and formamide, i.e., methylenediformamide.

The reaction temperature can be between about 0° C. and about 80° C., and preferably between about 10° C. and about 35° C., for either or both of the above hydrolysis and cyclization reactions. Reaction media other than HCl/water which may be used include sulphuric acid/water, perchloric acid/water, phosphoric acid/water, and various acidified organic-aqueous systems containing miscible alcohols, ketones, amides, and the like.

The concentration of reactants and acid may vary within wide limits, for example, on the basis of 100 ml. of water, the gram moles of the biscarbonyl compound is between about 0.05 and 25, preferably between 0.1 and 5, the bisamide reactant or its salt is between about 0.05 and about 25, preferably between 0.1 and 5, and sufficient acid should be used to effect complete hydrolysis and preferably form the imidazole salt. Generally, the moles of acid will be between about 0.5 to about 15 per 100 ml. of water although concentrations well outside of these limits may be employed, albeit, to no advantage.

The following table gives typical reactants and consequent products.

| R | $R_1$ | $R_2$ | $R_3$ | $A^-$ |
|---|---|---|---|---|
| H | $CH_3$ | $CH_2Cl$ | H | Cl |
| $C_6H_5$ | $C_2H_5$ | $CH_2Cl$ | H | Cl |
| H | $CH_2Cl$ | $CH_2Cl$ | H | Cl |
| $CH_3$ | $CH_2Cl$ | $CH_2Cl$ | H | $SO_4$ |
| $C_6H_{11}$ | $CH_3$ | $CH_2Cl$ | H | F |
| $C_6H_4$—4-Cl | $CH_3$ | $CH_2Cl$ | H | Br |
| $CH_3OCH_2$ | $CH_3$ | $CH_2OC_2H_5$ | $CH_3$ | Cl |
| $C_6H_4$—4-$OCH_3$ | $CH_3$ | $CH_2Cl$ | H | $SO_3CH_3$ |
| H | $CH_3$ | $CH_2OH$ | H | Cl |
| H | $CH_2OH$ | $CH_2OH$ | H | Cl |
| H | $CH_3$ | $CH_2Br$ | H | Cl |
| H | $CH_2Br$ | $CH_2Br$ | H | Cl |
| H | $CH_3$ | $CH_2Cl$ | $C_3H_7$ | Cl |
| H | $CH_3$ | $CH_2Cl$ | $C_6H_{11}$ | Cl |
| H | $CH_3$ | $CH_2Cl$ | $C_6H_5$ | Cl |
| H | $CH_3$ | $CH_2Cl$ | $CH_2OC_2H_5$ | Cl |
| H | $CH_3$ | $CH_2Cl$ | $CH_2Cl$ | Cl |
| $C_6H_5$ | $C_2H_5$ | $CH_2Cl$ | H | $SO_3CH_2C_6H_5$ |
| H | $CH_2Cl$ | $CH_2Cl$ | H | $SO_3C_6H_4$—p-$CH_3$ |
| H | $CH_2Cl$ | $CH_2Cl$ | H | $SO_3C_6H_4$—p-$CH_3$ |
| $C_6H_{11}$ | $CH_3$ | $CH_2Cl$ | H | $SO_3C_6H_4$—p-$CH_3$ |
| $C_6H_4$—4-Cl | $CH_3$ | $CH_2Cl$ | H | $SO_3C_6H_4$—p-$CH_3$ |
| $CH_3OCH_2$ | $CH_3$ | $CH_2OC_2H_5$ | $CH_3$ | $SO_3C_6H_4$—p-$CH_3$ |
| $CH_2C_6H_5$ | $CH_3$ | $CH_2OC_2H_5$ | $CH_3$ | $SO_3C_6H_4$—p-$CH_3$ |
| H | $CH_3$ | $CH_2Cl$ | H | $OCOCH_2C_6H_5$ |
| $C_6H_5$ | $C_2H_5$ | $CH_2Cl$ | H | $OCOCH_2C_6H_5$ |
| H | $CH_2Cl$ | $CH_2Cl$ | H | $OCOCH_2C_6H_4$—p-$CH_3$ |
| $C_6H_{10}$—4-Cl | $CH_2Cl$ | $CH_2Cl$ | H | $OCOC_3H_7$ |
| $C_6H_{11}$ | $CH_3$ | $CH_2Cl$ | H | $OCOC_3H_7$ |
| $C_6H_4$—4-Cl | $CH_3$ | $CH_2Cl$ | H | $OCOC_4H_9$ |
| $CH_3OCH_2$ | $CH_3$ | $CH_2OC_2H_5$ | $CH_3$ | $OCOC_6H_5$ |

The following preparations further illustrate the invention.

EXAMPLE 1

Diacetyl (2.66 g, 0.031 mole) was added to concentrated (6 N) hydrochloric acid (20 ml) with stirring. Methylene diformamide (3.0 g, 0.029 mole) was then added in small portions over about ten minutes, and the reaction mixture stirred at room temperature for two hours. The solution was then evaporated to dryness, the residue washed with acetone and the solid hydrochloride removed by filtration. Yield was 3.2 g of 4,5-dimethylimidazole hydrochloride (82% based on methylene diformamide) N.M.R. and I.R. spectra were consistent with structure and purity by High Pressure Liquid Chromatography (HPLC) was 100%.

EXAMPLE 2

Monochlorodiacetyl (3.54 g, 0.0294 mole) was dissolved in about 20 ml of concentrated hydrochloric acid at room temperature (20° C.). Methylene diformamide (3.0 g, 0.0294 mole) was then added in portions, over about ten minutes and slight exotherm to 28° C. occurred. The reaction mixture was then stirred for a further two hours, and excess hydrochloric acid removed by rotary evaporation. Residual crude chloromethyl methylimidazole hydrochloride was washed with acetone (three-four fifteen ml portions) and filtered.

Yields and assays for additional similar Examples 3–7 are shown in Table 1.

TABLE 1

| Example No. | Conc. (6N) HCl (ml) | Yield (g) | Yield (%) | HPLC* Assay Area % | HPLC* Assay Wt. % |
|---|---|---|---|---|---|
| 3 | 20 | 3.6 | 73 | 98 | 104 |
| 4 | 20 | 3.8 | 77 | 98 | 98 |
| 5 | 10 | 3.5 | 71 | 98 | 104 |
| 6 | 10 | 3.8 | 77 | — | — |
| 7 | 10 | 3.9 | 79 | 97 | 87 |

*Product submitted to HPLC in water whereupon product assays as hydrolysis product, hydroxymethyl methyl imidazole.

EXAMPLE 8

Reactions of Methylene Diformamide with Pyruvaldehyde

Pyruvic aldehyde (5.58 g, 40% by weight commercial solution) was dissolved in conc. hydrochloric acid (20 ml) and methylene diformamide (3.0 g) added. After stirring two hours at room temperature the solution was evaporated to give a brown oil. After washing with acetone the solid precipitate (3.0 g.) was removed by filtration. H.P.L.C. comparison with a pure sample of 4 methyl imidazole hydrochloride indicates the solid assay of 55% by weight, 4-methyl imidazole.

EXAMPLE 9

Reaction of Methylene Diformamide with Glyoxal

Glyoxal (4.45 g, 0.031 mole) was dissolved in conc. hydrochloric acid (20 ml) and treated with methylene diformamide (3.0 g) exactly as described above. Work-up as in Example 8 gave 3.0 g crude imidazole. Assay was 42% by weight imidazole, compared to a standard sample of imidazole hydrochloride.

EXAMPLE 10

4,5-Bis-Chloromethyl Imidazole Hydrochloride

Crude, α, α' dichlorobiacetyl (4.65, 0.03 mole) was admixed with hydrochloric acid (50 ml) containing methanol (10 ml), and methylene diformamide (3.06 g, 0.03 mole) was added over about five minutes. After stirring three hours at room temperature the solution was evaporated to dryness at reduced pressure. Treatment of the residue with hot acetone (30 ml) and filtering gave crude product (4.3 g, 71%).

A typical reaction step sequence for obtaining the intermediates and imidazole product which may be the salt of step 3 or the neutral product of step 4 is as follows:

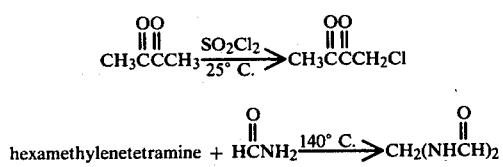

1.

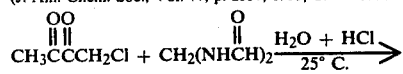

2.

(J. Am. Chem. Soc., Vol. 77, p. 2559, 1955; C. W. Sauer and R. J. Bruni)

3.

(according to present invention)

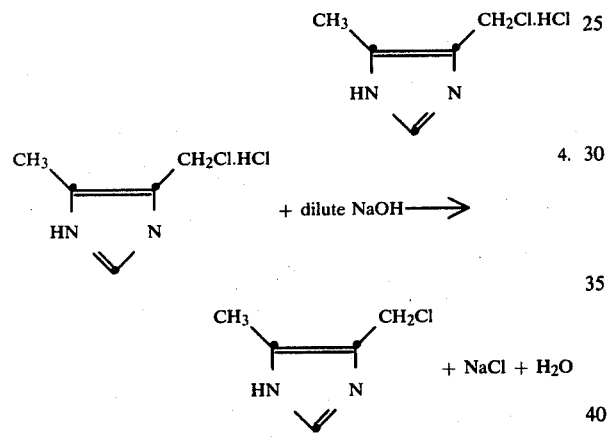

The invention has been described in detail with particular reference to certain preferred embodiments thereof, but it will be understood that variations and modifications can be effected within the spirit and scope of the invention.

We claim:

1. The process for preparing an imidazole of the formula

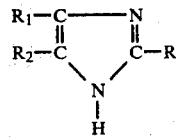

comprising contacting a diamine salt of the formula

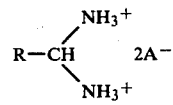

in concentrated HCl, $H_2SO_4$, $HClO_4$ or $H_3PO_4$ with a biscarbonyl compound of the structure

wherein $A^-$ is an anion equivalent of said HCl, $H_2SO_4$, $HClO_4$, or $H_3PO_4$, and R, $R_1$ and $R_2$ are each selected from hydrogen, an alkyl radical of 1 to 3 carbon atoms, and said alkyl radical substituted with 1 to 3 of halogen, hydroxy, lower alkoxy, lower alkoxycarbonyl, lower alkoxycarbonyloxy, carbamoyl, lower alkylcarbamoyl, lower dialkylcarbamoyl, lower alkylthio, or phenyl.

2. The process of claim 1 wherein the reaction temperature is between about 0° C. and about 80° C., and on the basis of 100 ml. of water, the gram moles of biscarbonyl compound is between about 0.05 and 25, the gram moles of bisamide reactant or its salt is between about 0.05 and about 25, and sufficient acid should be used to effect complete hydrolysis and form the imidazole salt.

3. The process of claim 2 wherein the gram moles of acid per 100 ml. of water in between about 0.5 and 15.

4. The process of claim 1 wherein $R_1$ and $R_2$ are each selected from methyl, chloromethyl and bromomethyl, and R is —H.

5. The process of claim 1 wherein the diamine salt is formed in situ from methylenediformamide.

* * * * *